(12) United States Patent
Wisniewski et al.

(10) Patent No.: US 8,158,380 B2
(45) Date of Patent: Apr. 17, 2012

(54) IMAGING AGENTS FOR PROTEIN MISFOLDING

(75) Inventors: Thomas Wisniewski, Staten Island, NY (US); Jaeki Min, Marietta, GA (US); Qian Li, Frederick, MD (US); Young-Tae Chang, Singapore (SG)

(73) Assignee: New York University, New York, NY (US)

( * ) Notice: Subject to any disclaimer, the term of this patent is extended or adjusted under 35 U.S.C. 154(b) by 1010 days.

(21) Appl. No.: 12/029,271

(22) Filed: Feb. 11, 2008

(65) Prior Publication Data
US 2010/0279340 A1    Nov. 4, 2010

Related U.S. Application Data

(60) Provisional application No. 60/900,329, filed on Feb. 9, 2007.

(51) Int. Cl.
*G01N 1/30* (2006.01)
*C07D 453/04* (2006.01)

(52) U.S. Cl. ................................. 435/40.5; 546/134
(58) Field of Classification Search ................ None
See application file for complete search history.

(56) References Cited

FOREIGN PATENT DOCUMENTS
JP    09255686 A  *  9/1997

OTHER PUBLICATIONS

Wikipedia, Benzene, Discovery History (2011).*

* cited by examiner

*Primary Examiner* — Yong Chu
(74) *Attorney, Agent, or Firm* — Browdy and Neimark, PLLC

(57) ABSTRACT

Charged and neutral small fluorescent molecules based upon the styryl scaffold are useful as imaging agents for misfolded proteins such as amyloid plaque. Charged molecules are prepared using pyrrolidine catalyzed reactions by solution-phase synthesis. Neutral styryl molecules are prepared using acetic anhydride catalyzed reactions, Horner-Emmons reactions or Wittig reactions.

3 Claims, 14 Drawing Sheets

Method A: Solution-phase synthesis of charged styryl compounds
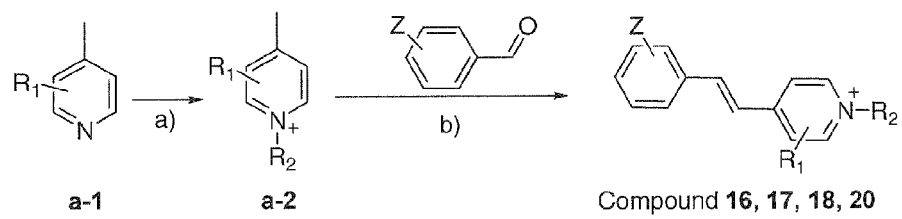
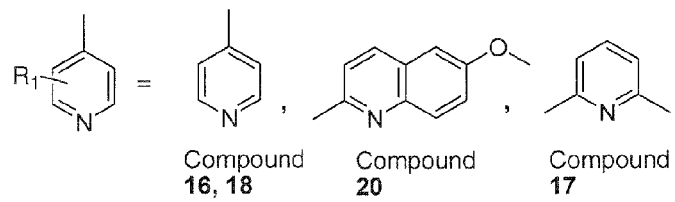
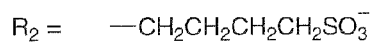
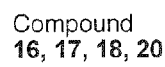
Compound
16, 17, 18, 20
Figure 1: Solution-phase synthesis of charged styryl compounds: a) 1,4-butane sultone, Ethylacetate, reflux, overnight; b) pyrrolidine, ethanol, reflux, 3 hours.

Method B: Synthesis of neutral styryl compound using acidic catalyzed reaction
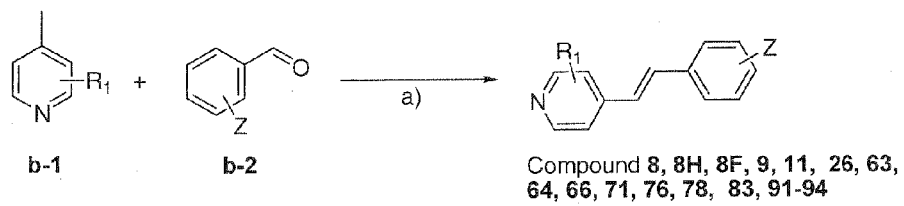
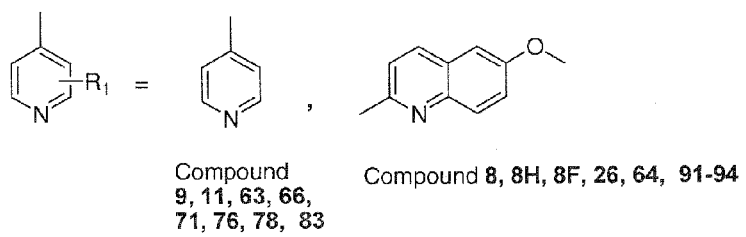
Figure 2: Synthesis of neutral styryl compounds using acidic catalyzed reaction: a) Acetic anhydride, 130°C, overnight or microwave 3 min Method C: Synthesis of neutral styryl compound using Horner-Emmons reaction
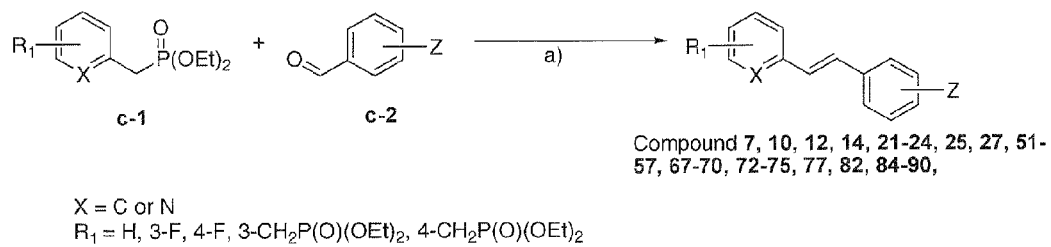
Compound 7, 10, 12, 14, 21-24, 25, 27, 51-57, 67-70, 72-75, 77, 82, 84-90,
X = C or N
$R_1$ = H, 3-F, 4-F, 3-$CH_2$P(O)(OEt)$_2$, 4-$CH_2$P(O)(OEt)$_2$
Figure 3: Synthesis of neutral styryl compounds using Horner-Emmons reaction: a) NaH, DMF, 1300W microwave 40 sec.

Method D: Synthesis of neutral styryl compounds using Wittig reaction
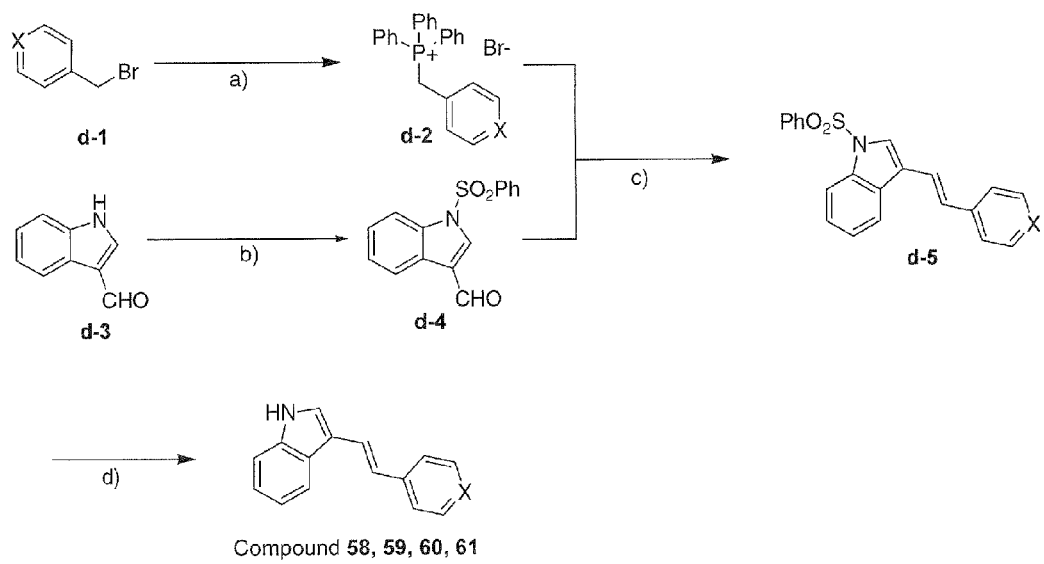
Compound 58, 59, 60, 61
X = C or N
Figure 4: a) PPh$_3$, xylene, microwave 40 sec; b) PhSO$_2$Cl, K$_2$CO$_3$, DCM, reflux 2h; c) n-BuLi, THF, -10°C to r.t., 12h; c) NaOH 3eq, MeOH, reflux, 12h

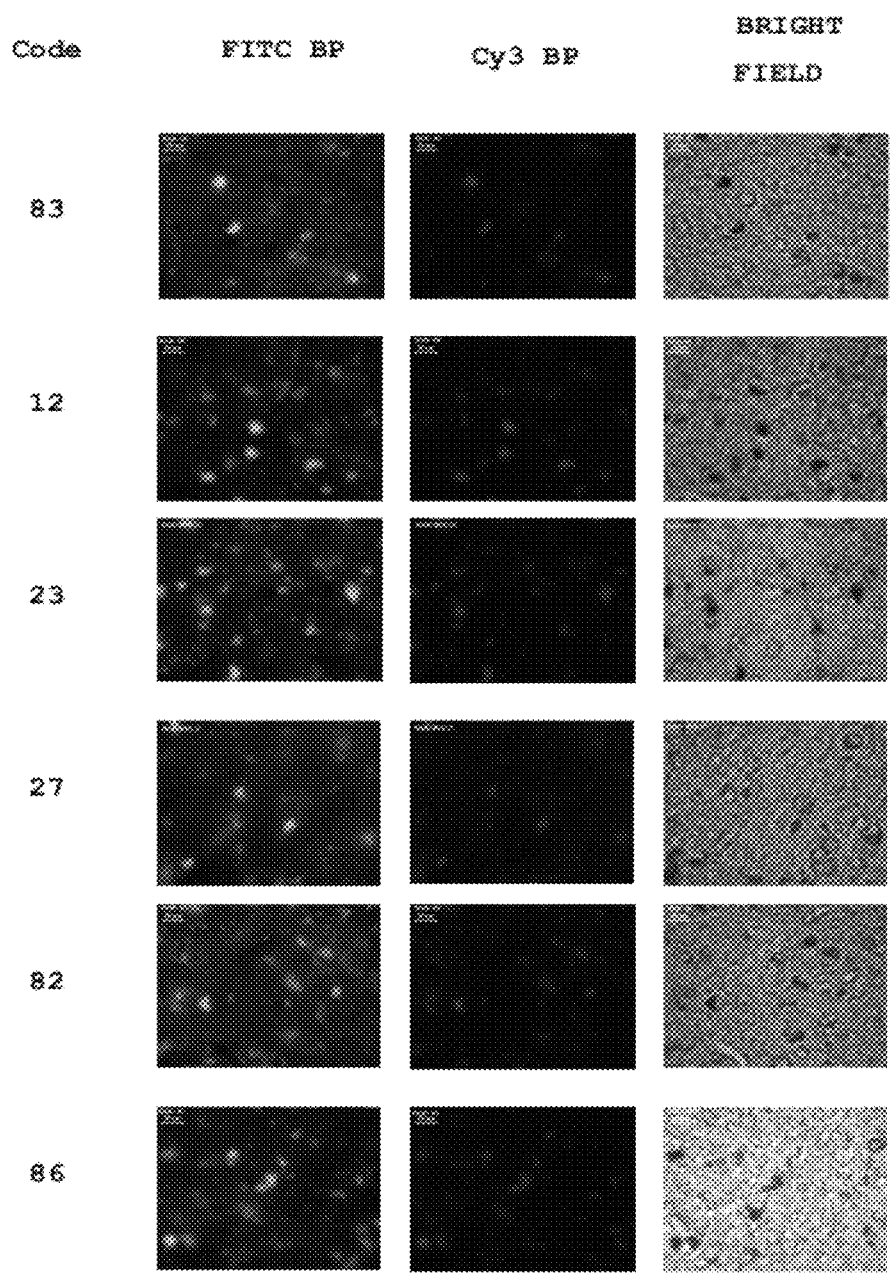
Figure 5A: DAB Staining in AD Human Brain Tissue

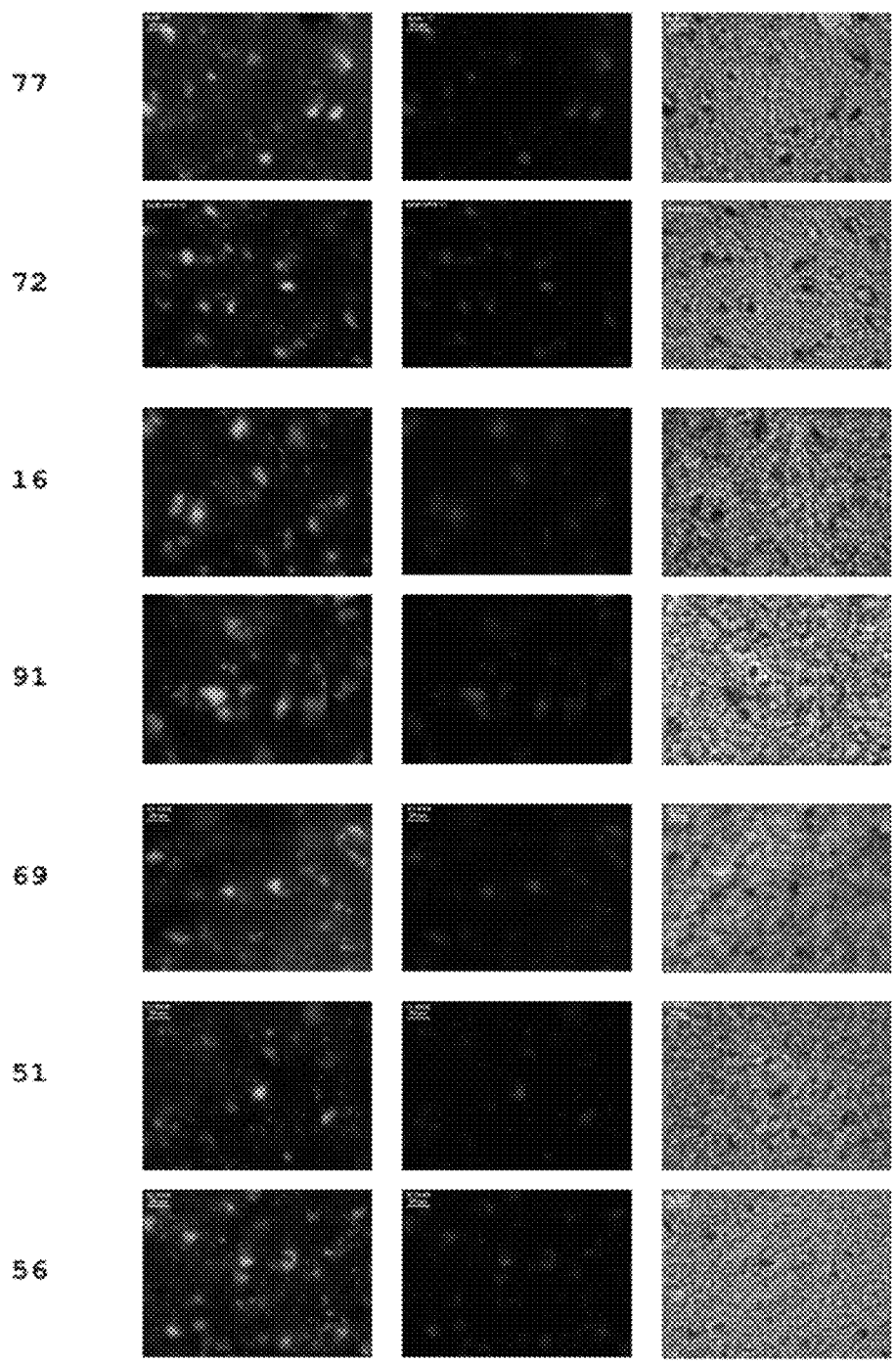

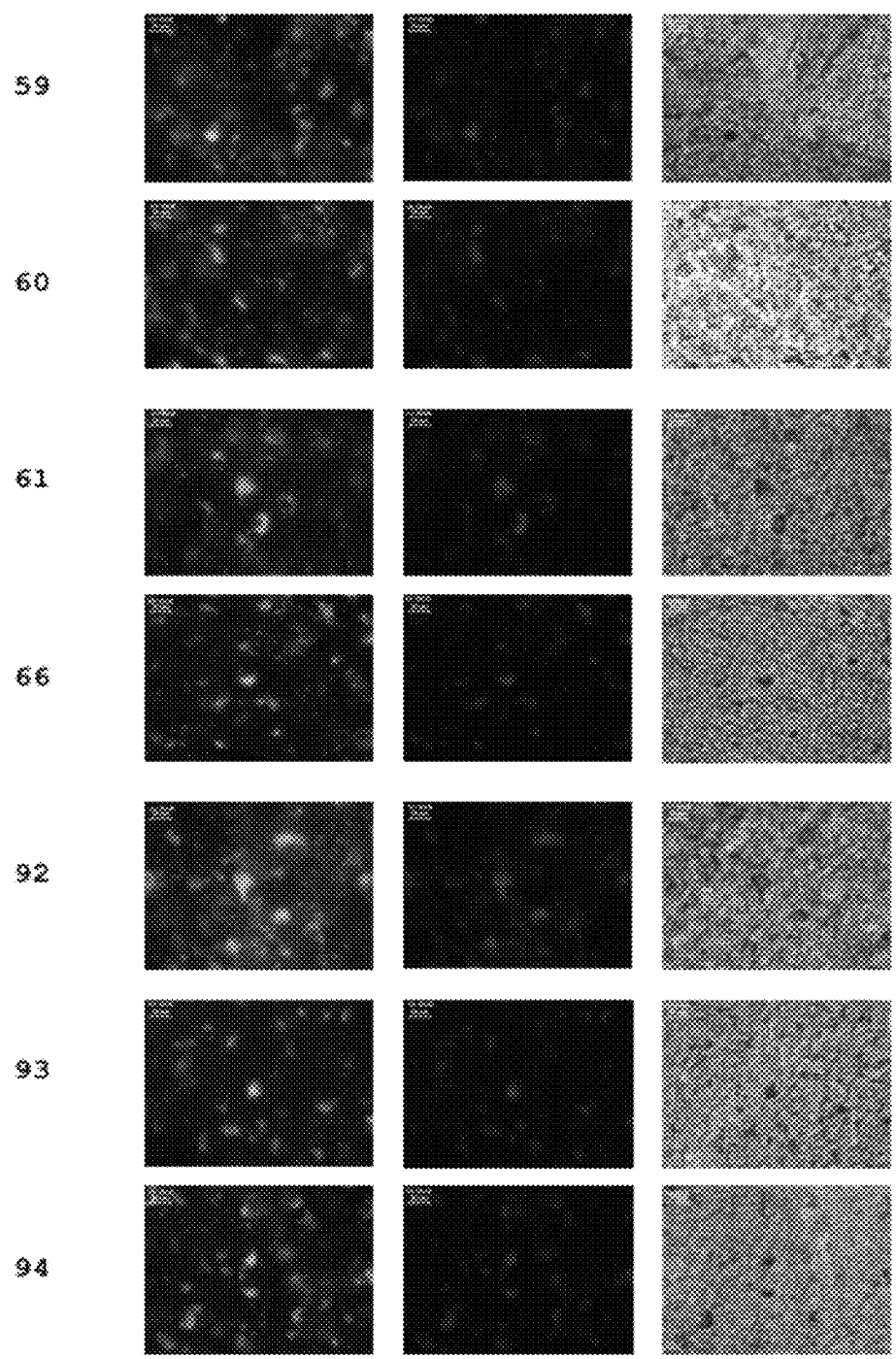

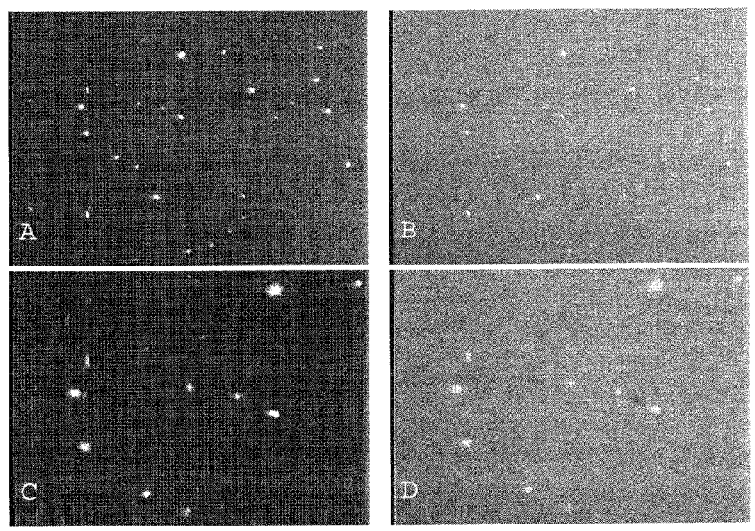
Figure 6: Figure 6 A and C show Thioflavin S stained sections of amyloid deposits in AD model mice at 50 and 100x magnification. B and D show sequential sections stained with compound 8 showing an almost perfect match.

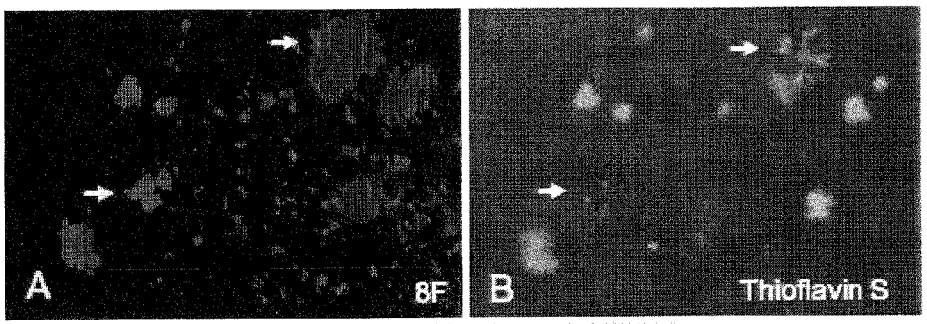

Figure 7 shows *in vivo* staining using compound 8F and matching controls. 2A shows the staining after *in vivo* injection with compound 8F in AD mice. The mouse was sacrificed 24 hr after injection (as described above) and sections viewed under a fluorescent microscope. This shows that 8F is able to cross the BBB and *in vivo* label amyloid plaques. In 2B a match is shown with Thioflavin applied directed to the section. 2C shows the Aβ immunohistochemistry of a matching section to 2A.

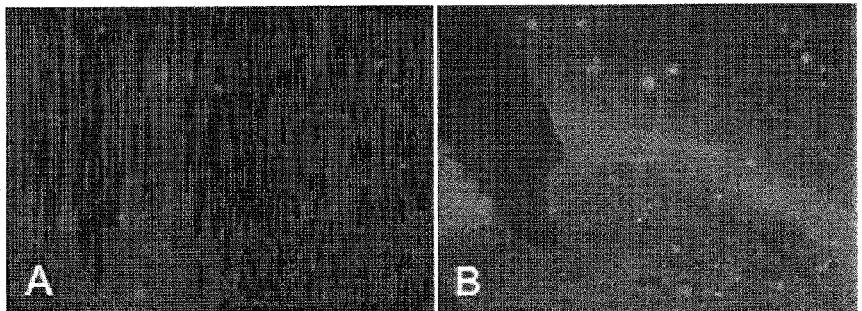

Figure 8: In Vivo staining using compound 23

Figure 8: Shows *in vivo* staining using compound 23 and matching controls. 3A shows the staining after *in vivo* injection with compound 23 in AD mice. The mouse was sacrificed 24 hr after injection (as described above) and sections viewed under a fluorescent microscope. This shows that 23 is able to cross the BBB and *in vivo* label amyloid plaques. In 3B a match is shown with Thioflavin applied directed to the section. 3C shows the Aβ immunohistochemistry of a matching section to 3A.

Figure 9: Two Photon In vivo Image
of Amyloid Plaque Using
Compound 23

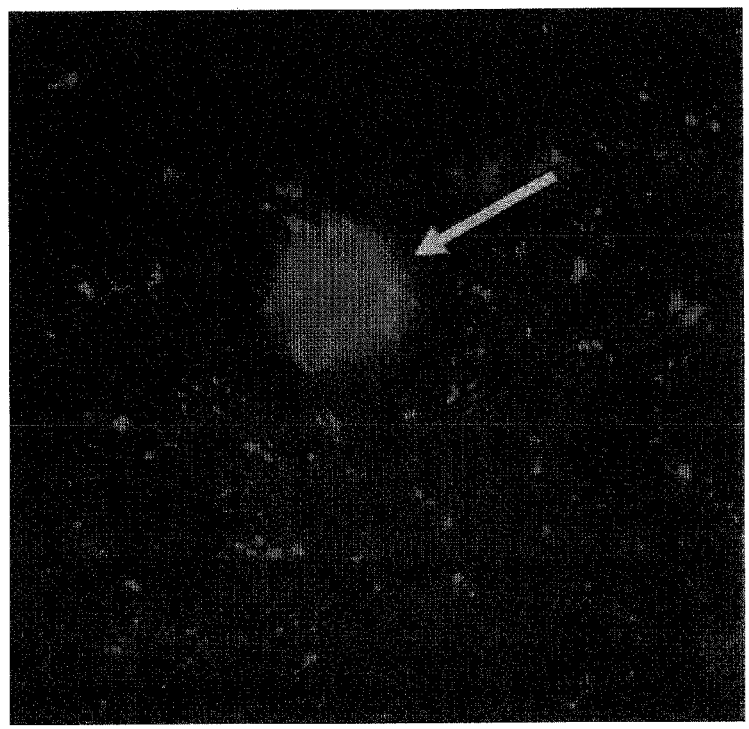

Figure 9 shows the labeling of an amyloid plaque using compound 23. The image was obtained *in vivo* following an IP injection of compound 23 in an AD mouse, using methods described above and as we have previously published[25]. This definitively shows the compound is able to cross the BBB and label plaques *in vivo*.

Figure 10: Two Photon In Vivo Imaging of Amyloid Plaques using Compound 8

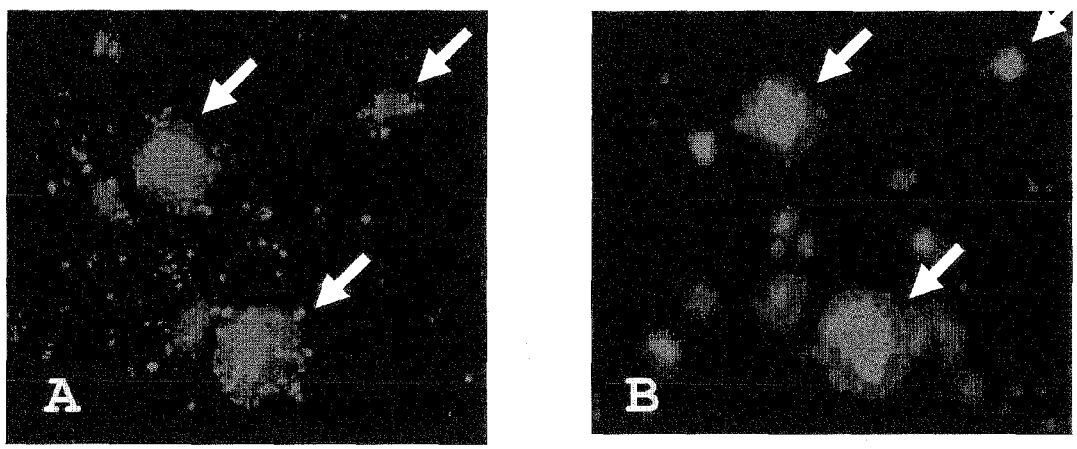

Figure 10 shows the in vivo labeling of amyloid plaques using compound 8 in A. The image was obtained in vivo following an IP injection of compound 8 in an AD model transgenic mouse, using methods described above and as we have previously published [25]. In B, Congo red staining was applied in vivo directly to the animal's brain surface. The arrows show the excellent co-localization between the in vivo labeling using compound 8, which crossed the BBB and the Congo red, which is a standard amyloid stain (but does not cross the BBB and is toxic).

Figure 11: MTT Assay for Toxicity using Compounds 8 and 23

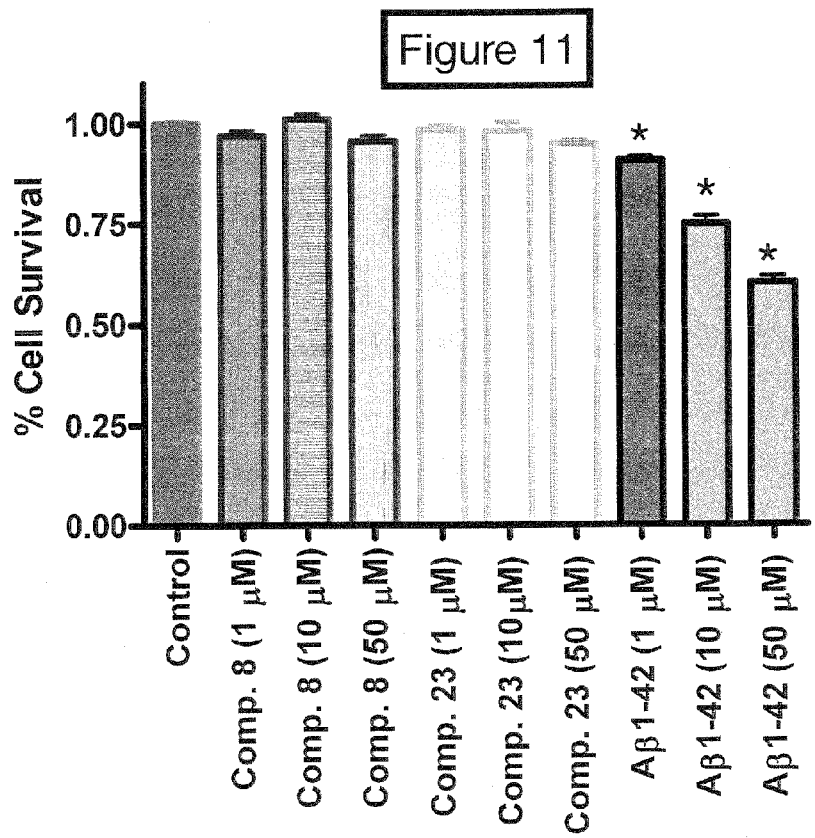

Figure 11 shows a MTT toxicity assay using a SK-N-SH human neuroblastoma cell line. As expected Aβ 1-42 demonsrates toxicity as seen by reduced cell survival at a concentration of 1 to 100 µM in a dosage dependent manner ( * $p<0.01$ versus control untreated cells). Compounds 8 and 23 show no toxicity at a concentration of 1 to 100 µM (no statistically significant difference between compounds 8 and 23 at any concentration versus control).

IMAGING AGENTS FOR PROTEIN MISFOLDING

CROSS-REFERENCE TO RELATED APPLICATIONS

This application claims priority under 35 U.S.C. §119(e) from U.S. provisional application no. 60/900,329 filed Feb. 9, 2007.

FIELD OF THE INVENTION

The present invention relates to compounds and methods for imaging misfolded proteins.

BACKGROUND OF THE INVENTION

Fluorescent sensors and probes have attracted attention because of their high sensitivity and exceptional ease of handling relative to their radioactive counterparts. Combinatorial chemistry is now widely used in the medicinal/pharmaceutical field and in chemical biology for the discovery of new biologically active molecules or drug candidates. The application of this method to fluorescent dyes is still quite new. A few early examples include oligopyridines, coumarins, oligonucleotides, and conjugated polymers. Application Ser. No. 10/656,875 discloses the first combinatorial wide-color-range fluorescent styryl library by solution-phase chemistry and their potential application as organelle-specific probes. Application Ser. No. 11/104,451 discloses another group of compounds that can be used as fluorescent dyes.

Unfortunately, it has been discovered that positively charged compounds cannot stain brain tissue to identify misfolded proteins.

Amyloids represent a case of protein misfolding leading to the formation of ordered secondary structures rich in cross β-sheets, which are present as fibrillar deposits in tissues.[6] Amyloid formation had been associated with a large number of protein misfolding diseases including type II diabetes, Alzheimer's, Parkinson's, Huntington's, mad-cow disease, and others.[7,8] Among the many amyloidoses, Alzheimer's disease (AD) is the fourth leading cause of death in the United States, and the most common cause of adult-onset dementia.[9,10] The deposition of β-amyloid (Aβ) aggregates in brain tissue is one of the hallmark characteristics in AD and the efficient imaging agents of amyloid plaque for the diagnosis of AD would be particularly helpful in diagnosing this disease while the patient is still alive.[11]

SUMMARY OF THE INVENTION

It is an object of the present invention to overcome the aforesaid deficiencies in the prior art.

It is another object of the present invention to provide fluorescent small molecules based on the styryl scaffold.

It is a further object of the present invention to provide fluorescent small molecules based on the styryl scaffold that can be used for imaging misfolded proteins.

It is yet another object of the present invention to provide fluorescent small molecules that can be used as imaging agents for amyloid plaques in vivo as well as in vitro.

The compounds of the invention comprise a group of novel fluorescent small molecules based on the styryl scaffold. The compounds are classified into two groups: charged and neutral styryl compounds with a total of 68 members. Both of these groups include monostyryl and distyryl subgroups. Of these molecules, thirteen are positively charged molecules; the remaining molecules are neutral.

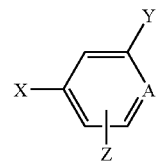

Formula I

Wherein
A=C, N—$R_1$, Here, $R_1$=none, —$CH_2CH_2CH_2CH_2SO_3^-$
X=H, —CH=CH-Q, Here, Q=substituted phenyl, substituted or unsubstituted indolyl, substituted or unsubstituted naphthyl, aryl substituted furan
Y=Z=H, Br, F, I, —CH=CH—P, Here, P=substituted phenyl, substituted or unsubstituted indolyl, substituted or unsubstituted naphthyl

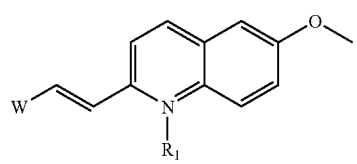

Formula II

Wherein
R1=none, —$CH_2CH_2CH_2CH_2SO_3^-$
W=substituted or unsubstituted biphenyl, naphthyl, aryl substituted furan A "substituent" as used herein includes alkyl, cycloalkyl, cycloaryl, aryl, heteroaryl, optionally substituted with 1 or more, preferably 1 to 3, substituents selected from halo, haloalkyl, and alkyl, arylalkyl, heteroarylalkyl, alkenyl containing 1 to 2 double bonds, alkynyl containing 1 to 2 triple bonds, halo, hydroxy, polyhaloalkyl, preferably trifluoromethyl, formyl, alkylcarbonyl, arylcarbonyl, optionally substituted with 1 or more, preferably 1 to 3, substituents selected from halo, haloalkyl, alkyl, heteroarylcarbonyl, carboxyl, alkoxycarbonyl, aryloxycarbonyl, aminocarbonyl, alkylaminocarbonyl, dialkylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, amido, nitro, mercapto, alkylthio, arylthio, perfluoroalkylthio, thiocyano, isothiocyano, alkylsufinyl, alkylsulfonyl, arylsulfinyl, arylsulfonyl, aminosulfonyl, alkylaminosulfinyl, dialkylaminosulfonyl, and arylaminosulfonyl.

As used herein, alkyl, alkenyl and alkynyl carbon chains, if not specified, contain from 1 to 20 carbon atoms, preferably from 1 to 16 carbon atoms, and are straight or branched. Alkenyl carbon chains of from 1 to 20 carbon atoms preferably contain 1 to 8 double bonds; the alkenyl carbon chains of 1 to 16 carbon atoms preferably contain from 1 to 5 double bonds.

Alkynyl carbon chains of from 1 to 20 carbon atoms preferably contain 1 to 8 triple bonds, and the alkynyl carbon chains of 1 to 16 carbon atoms preferably contain 1 to 5 triple bonds. The alkyl, alkenyl, and alkynyl groups may be optionally substituted, with one or more groups, preferably alkyl group substituents that may be the same or different. As used herein, lower alkyl, lower alkenyl, and lower alkynyl refer to carbon chains having fewer than or equal to about 6 carbon atoms.

As used herein an alkyl group substituent includes halos, haloalkyl, preferably halo lower alkyl, aryl, hydroxy, alkoxy, aryloxy, alkoxy, alkylthio, arylthio, aralkyloxy, aralkylthio, carboxy, alkoxycarbonyl, oxo, and cycloalkyl.

For the present invention, "cyclic" refers to cyclic groups preferably containing from 3 to 19 carbon atoms, preferably 3 to 10 members, more preferably 5 to 7 members. Cyclic groups include hetero atoms, and may include bridged rings, fused rings, either heterocyclic, cyclic, or aryl rings.

The term "arylalkyl" as used herein refers to an alkyl group which is substituted with one or more aryl groups. Examples of arylalkyl groups include benzyl, 9-fluorenylmethyl, naphthylmethyl, diphenylmethyl, and triphenylmethyl.

"Cycloalkyl" as used herein refers to a saturated mono- or polycyclic ring system, preferably of 3 to 10 carbon atoms, more preferably from 3 to 6 carbon atoms. Cycloalkenyl and cycloalkynyl refer to mono- or multicyclic ring systems that respectively include at least one double bond and at least one triple bond. Cycloalkenyl and cycloalkynyl groups may preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups may be composed of one ring or two or more rings which may be joined together in a fused, bridged, or spiro-connected fashion, and may be optionally substituted with one or more alkyl group substituents.

The term "heteroaryl" for purposes of the present application refers to a monocyclic or multicyclic ring system, preferably about 5 to about 15 members, in which at least one atom, preferably 1 to 3 atoms, is a heteroatom, that is, an element other than carbon, including nitrogen, oxygen, or sulfur atoms. The heteroaryl may be optionally substituted with one or more, preferably 1 to 3, aryl group substituents. Exemplary heteroaryl groups include, for example, furanyl, thienyl, pyridyl, pyrrolyl, N-methylpyrrolyl, quinolyinyl and isoquinolinyl.

The term "heterocyclic" refers to a monocyclic or multicyclic ring system, preferably of 3 to 10 members, more preferably 4 to 7 members, where one or more, preferably 1 to 3, of the atoms in the ring system is a heteroatom, i.e., an atom that is other than carbon, such as nitrogen, oxygen, or sulfur. The heterocycle may be optionally substituted with one or more, preferably 1 to 3, aryl group substituents. Preferred substituents of the heterocyclic group include hydroxy, alkoxy, halo lower alkyl. The term heterocyclic may include heteroaryl. Exemplary heterocyclics include, for example, pyrrolidinyl, piperidinyl, alkylpiperidinyl, morpholinyl, oxadiazolyl, or triazolyl.

The nomenclature alkyl, alkoxy, carbonyl, etc, is used as is generally understood by those of skilled this art. As used herein, aryl refers to saturated carbon chains that contain one or more carbon atoms; the chains may be straight or branched or include cyclic portions or may be cyclic.

The term "halogen" or "halide" includes F, Cl, Br, and I. This can include pseudohalides, which are anions that behave substantially similarly to halides. These compounds can be used in the same manner and treated in the same manner as halides. Pseudohalides include, but are not limited to, cyanide, cyanate, thiocyanate, selenocyanate, trifluoromethyl, and azide.

The term "haloalkyl" refers to a lower alkyl radical in which one or more of the hydrogen atoms are replaced by halogen, including but not limited to, chloromethyl, trifluoromethyl, 1-chloro-2-fluoroethyl, and the like.

"Haloalkoxy" refers to RO— in which R is a haloalkyl group.

The term "sulfinyl" refers to —S(O)—. "sulfonyl" refers to —S(O)$_2$—.

"Aminocarbonyl" refers to —C(O)NH$_2$.

"Alkylene" refers to a straight, branched, or cyclic, preferably straight or branched, bivalent aliphatic hydrocarbon group, preferably having from 1 to about 20 carbon atoms. The alkylene group is optionally substituted with one or more alkyl group substituents. There may be optionally inserted along the alkylene group one or more oxygen, sulfur, or substituted or unsubstituted nitrogen atoms, wherein the nitrogen substituent is alkyl. Exemplary alkylene groups include methylene, ethylene, propylene, cyclohexylene, methylenedioxy, and ethylenedioxy. The term "lower alkylene" refers to alkylene groups having from 1 to 6 carbon atoms. Preferred alkylene groups are lower alkylene, with alkylene of 1 to 3 atoms being particularly preferred.

The term "alkenylene" as used herein refers to a straight, branched or cyclic, preferably straight or branched, bivalent aliphatic hydrocarbon group, preferably having from about 1 to 20 carbon atoms and at least one double bond. The alkenylene group is optionally substituted with one or more alkyl group substituents. There may be optionally inserted along the alkenylene group one or more oxygen, sulfur, or substituted or unsubstituted nitrogen atoms, where the nitrogen substituent is alkyl as previously described.

As used herein, "alkynylene" refers to a straight, branched or cyclic bivalent aliphatic hydrocarbon group having from 1 to about 20 carbon atoms and at least one triple bond. The alkynylene group is optionally substituted with one or more alkyl group substituents. There may be optionally inserted along the alkynylene group one or more oxygen, sulfur, or substituted or unsubstituted nitrogen atoms, where the nitrogen substituent is alkyl. The term "lower alkynylene" refers to alkynylene groups having from 2 to 6 carbon atoms.

The term "arylene" as used herein refers to a monocyclic or polycyclic bivalent aromatic group preferably having from 1 to 20 carbon atoms and at least one aromatic ring. The arylene group is optionally substituted with one or more alkyl group substituents. There may be optionally inserted around the arylene group one or more oxygen, sulfur, or substituted or unsubstituted nitrogen atoms, where the nitrogen substituent is alkyl.

"Heteroarylene" refers to a bivalent monocyclic or multicyclic ring system, preferably of about 5 to about 15 members, wherein one or more of the atoms in the ring system is a heteroatom. The heteroarylene may be optionally substituted with one or more aryl group substituents.

As used herein, "alkylidene" refers to a bivalent group, such as =CR'R", which is attached to one atom of another group, forming a double bond. "Arylalkylidene" refers to an alkylidene group in which either R' or R" is an aryl group.

As used herein, when any particular group, such as phenyl or pyridyl, is specified, this means that the group is substituted or unsubstituted. Preferred substituents, where not specified, are halo, halo lower alkyl, and lower alkyl.

The term "library" refers to a collection of diverse compounds, in the present case, based upon a styryl scaffold.

Four different methods have been used to synthesize these compounds. The sulfonate charged molecules were prepared using pyrrolidine catalyzed reactions in solution phase synthesis, Method A. Neutral styryl molecules were prepared using acetic anhydride catalyzed reactions, Horner-Emmons reactions or Wittig reactions, Methods B, C or D. Unless noted otherwise, all compounds were purified by recrystallization, preparative TLD or column chromatography on silica gel. The final products were characterized by LC-MS and NMR.

BRIEF DESCRIPTION OF THE DRAWINGS

FIG. 1 illustrates Method A for synthesizing charged molecules according to the present invention.

FIG. 2 illustrates Method B for synthesizing neutral molecules according to the present invention.

FIG. 3 illustrates Method C for synthesizing neutral molecules according to the present invention.

FIG. 4 illustrates Method D for synthesizing neutral molecules according to the present invention.

FIGS. 5A-5D show the results of DAB staining in AD human brain tissue for various compounds from Table 1.

FIGS. 6A and 6C show Thioflavin S stained sections of amyloid deposits in AD model mice at 50 and 100× magnification. FIGS. 6B and 6D show sequential sections stained with compound 8, showing an almost perfect match.

FIG. 7 shows in vivo staining using compound 8F and matching controls. FIG. 7A shows the staining after in vivo injection with compound 8F in AD mice. The mouse was sacrificed 24 hours after injection as described below, and sections were viewed under a fluorescent microscope. This shows that compound 8F is able to cross the blood brain barrier and label amyloid plaques in vivo. In FIG. 7B a match is shown with Thioflavin applied directed to the section. FIG. 7C shows the Aβ immunohistochemistry of a matching section to FIG. 7A.

FIG. 8 shows in vivo staining using compound 23 and matching controls. FIG. 8A shows the staining after in vivo injection with compound 23 in AD mice. The mouse was sacrificed 24 hours after injection, as described below, and sections were viewed under a fluorescent microscope. This shows that compound 23 is able to cross the blood brain barrier and in vivo label amyloid plaques. In FIG. 3B, a match is shown with Thioflavin applied directly to the section. FIG. 8C shows the Aβ immunohistochemistry of a matching section to FIG. 8A.

FIG. 9 shows the labeling of an amyloid plaque using compound 23. The image was obtained in vivo following an intraperitoneal injection of compound 23 into an AD mouse, using methods described below. This figure definitely shows that the compound is able to cross the blood brain barrier and label plaques in vivo.

FIG. 10A shows in vivo imaging of amyloid plaques using compound 8. FIG. 10B shows co-localization between the in vivo labeling using compound 8 and Congo red.

FIG. 11 shows a MTT toxicity assay using an SK-N-Sh human neuroblastoma cell line.

DETAILED DESCRIPTION OF THE INVENTION

Figure 5B:
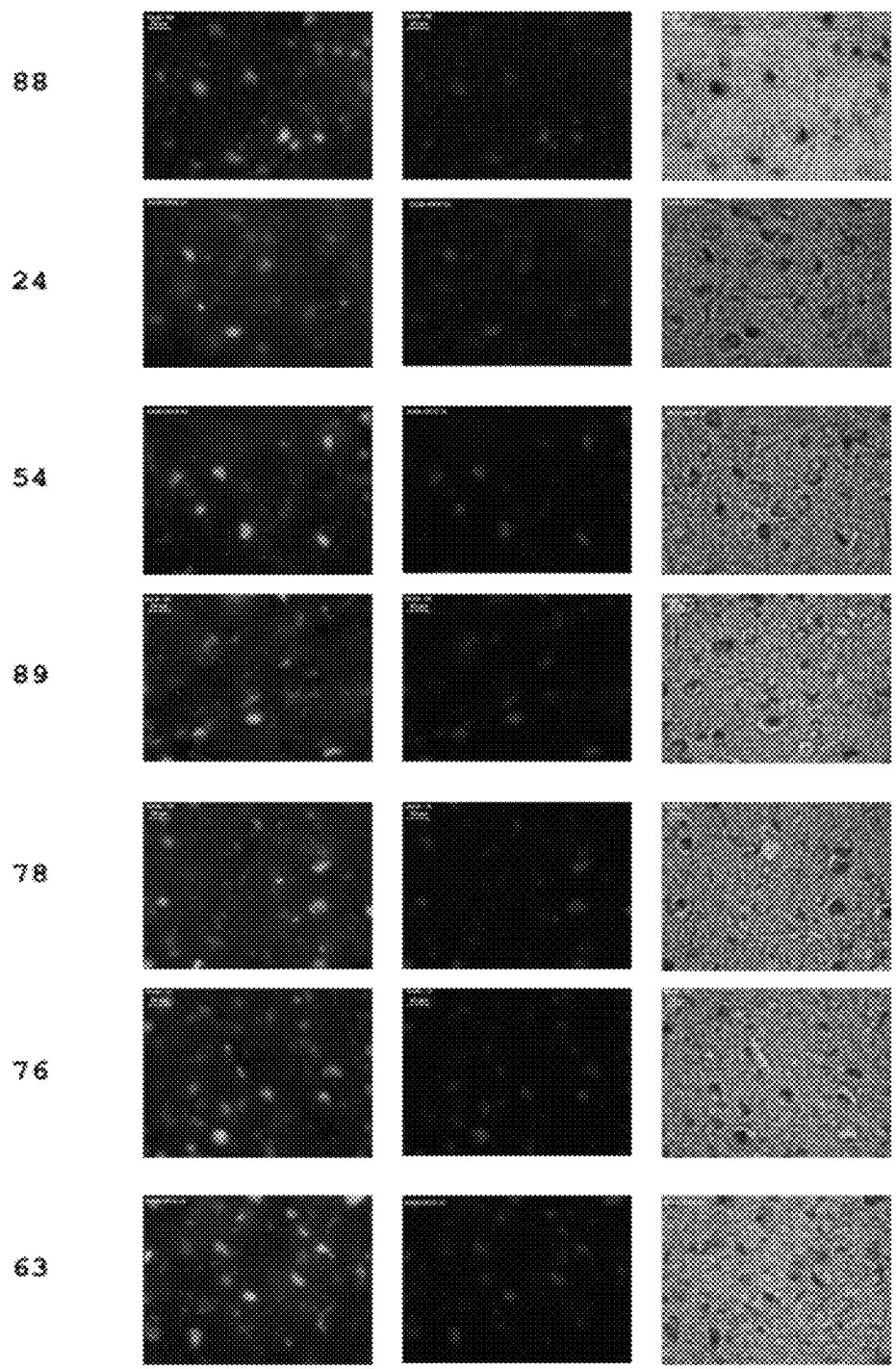

Method A was used to synthesize charged molecules using pyrrolidine catalyzed reactions. Methods B, C and D were used to synthesize neutral molecules.

The following non-limiting examples illustrate methods of preparing compounds according to the present invention.

Pyridine derivatives a-1 (2.04 mmol, structure shown in scheme) and 1,4-butane sultone (2.14 mmol) in ethyl acetate were refluxed overnight. After it was cooled down to room temperature, the pyridium substituted product a-2 was crystallized out. The crystals were filtered and washed with ethyl acetate three times, then dried. This product (0.08 mmol) was dissolved in 100% ethanol and different aldehyde (0.15 mmol) was added and refluxed for 3 hours. The reaction solution was then cooled down to −20° C. Final product (4 compounds) was purified by preparative TLC on silica gel (MC:MeOH=10:1).

4-Picoline or 6-methoxy quinaldine b-1 (0.12 mmol) and a different aldehyde were dissolved in acetic anhydride (5 mL). The reaction solution was stirred at 130° C. overnight. For the microwave irradiation reaction, two drops (about 20 uL each) of acetic anhydride was added into the starting material mixture. No solvent was used. The reaction mixture was irradiated at 1300 W microwave for 3 minutes. The reaction mixture was then washed by ethyl acetate and final product (17 compounds) was purified by column chromatography on silica gel (ethyl acetate:hexane=1:10). Yield from 20% to 80%.

To phosphonate c-1 (0.4 mmol) in DMF (5 mL) was added NaH (0.6 mmol). To this aromatic aldehyde c-2 (0.48 mmol) in DMF (2 mL) was added and the mixture was subjected to MW using a domestic microwave oven operated at 1300 W for 40 sec. After cooling, the product was extracted with ethyl acetate and dried over $MgSO_4$. The extract was filtered and the filtrate was evaporated under reduced pressure to leave the crude product. The final product (34 Compounds) was purified by column chromatography on silica gel (ethyl acetate: hexane=1:4).

A mixture of benzyl bromide d-1 (2 mmol) and triphenylphosphine (2 mmol) in xylene was subjected to MW using a domestic microwave oven operated at 1300 W for 40 sec. After cooling, the phosphonium salts were collected by filtration. To this phosphonium salts (0.5 mmol) in THF (10 mL) was added dropwise 1.6 M BuLi (0.5 mmol) at −10° and stirred at −10° to rt for 3.5 h. And then N-sulfonylated indolyl-3-carboxaldehyde d-4 was added and the reaction mixture was stirred for 12 h. The reaction mixture was extracted with ethyl acetate and washed the organic layer with water. The combined organic extract was dried over $MgSO_4$ and evaporated to give compound d-5, which was purified by column chromatography (ethyl acetate:hexane=1:4). To compound d-5 (0.3 mmol) in MeOH (5 mL) was added 3 N NaOH (1 mL) and refluxed for twelve hours. The reaction mixture was evaporated and the residue was extracted with ethyl acetate. The organic phase was dried over MgSO4 and filtered. The filtrated was purified by column chromatography (ethyl acetate:hexane=1:2) to give product (four compounds).

TABLE 1

Summary of 68 compounds structure, synthetic method, purity and synthetic notes

| Num. | Code | structure | method | % purity | Synthetic note |
|---|---|---|---|---|---|
| *Charged styryl compounds* | | | | | |
| 1 | 18 | 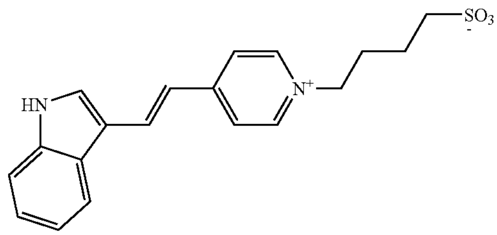 | A | 95 | |
| 2 | 20 | 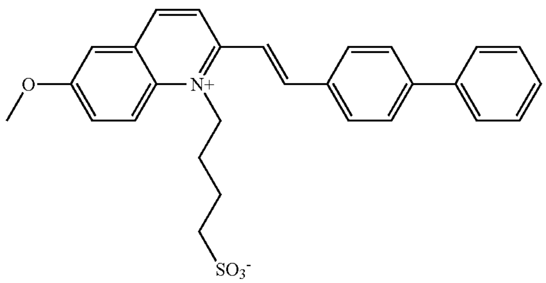 | A | 70 | |
| 3 | 16 | 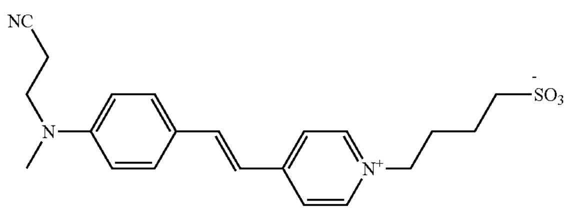 | A | 99 | |
| 4 | 17 | 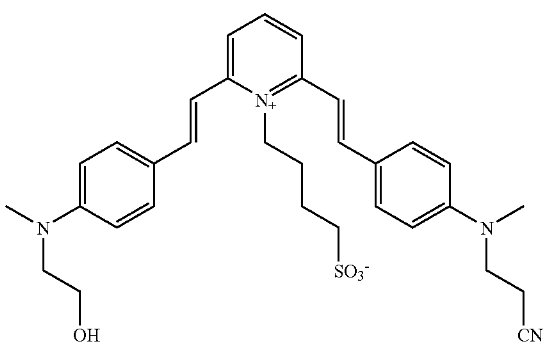 | A | 95 | |
| *Neutral Monostyryl Compounds* | | | | | |
| 5 | 58 | 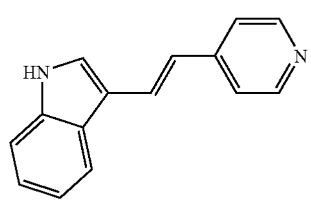 | D | 65 | Wittig reagent was made from 2-bromomethyl pyridine |
| 6 | 51 | 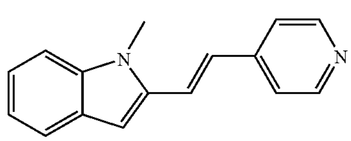 | C | 60 | Phosphonate was made from 2-bromomethyl pyridine |

TABLE 1-continued

Summary of 68 compounds structure, synthetic method, purity and synthetic notes

| Num. | Code | structure | method | % purity | Synthetic note |
|---|---|---|---|---|---|
| 7 | 9 | 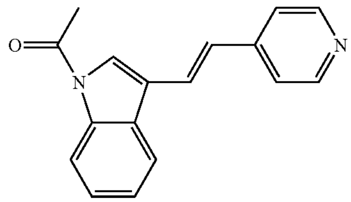 | B | 85 | Acetic anhydride heating condition. Acetylated product was purified. The acetyl group was later removed as shown as compound 14 |
| 8 | 56 | 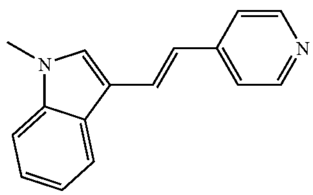 | C | 50 | Phosphonate was made from 2-bromomethyl pyridine |
| 9 | 60 | 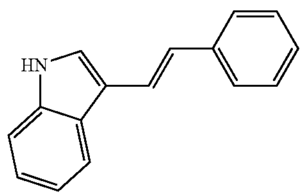 | D | 65 | |
| 10 | 53 | 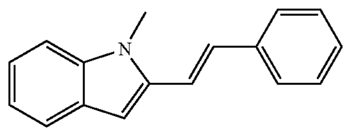 | C | 99 | |
| 11 | 57 | 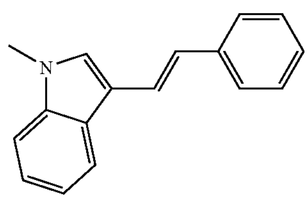 | C | 99 | |
| 12 | 8 | 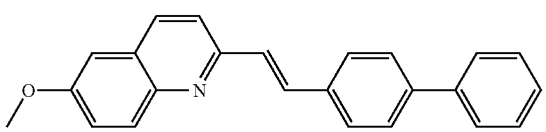 | B | 99 | Acetic anhydride heating condition |
| 13 | 8H | 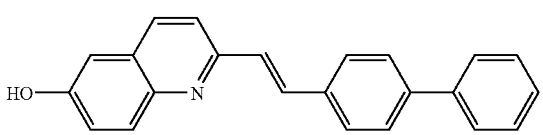 | B | 99 | 6-position hydroxy group was acetylated after the reaction. It was removed by $NaOCH_3$ in THF. Microwave reaction |
| 14 | 8F | 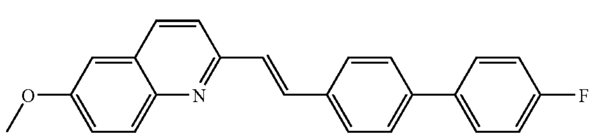 | B | 99 | Acetic anhydride heating condition |
| 15 | 26 | 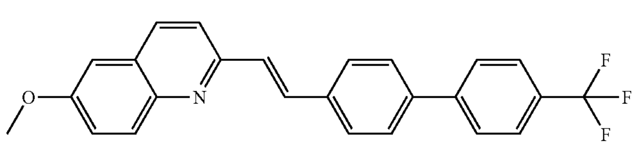 | B | 70 | Acetic anhydride heating condition |

TABLE 1-continued

Summary of 68 compounds structure, synthetic method, purity and synthetic notes

| Num. | Code | structure | method | % purity | Synthetic note |
|---|---|---|---|---|---|
| 16 | 94 | 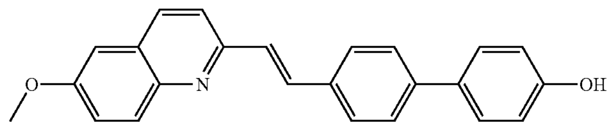 | B | 70 | Acetic anhydride heating condition |
| 17 | 91 | 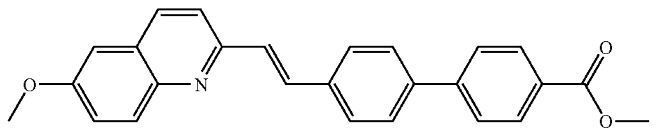 | B | 85 | Acetic anhydride heating condition |
| 18 | 92 | 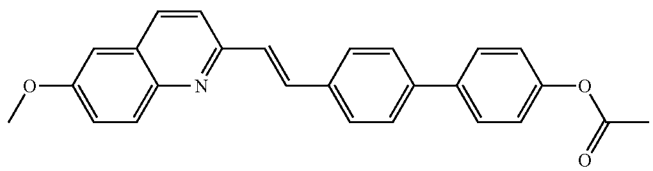 | B | 95 | Acetic anhydride heating condition |
| 19 | 93 | 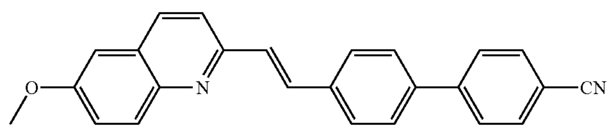 | B | 85 | Acetic anhydride heating condition |
| 20 | 64 | | B | 85 | Acetic anhydride heating condition |
| 20 | 11 | | B | 90 | Acetic anhydride heating condition |
| 22 | 82 | 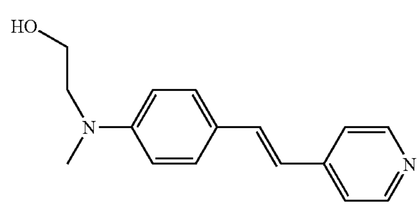 | C | 60 | hydroxy group was acetylated after reaction, and it was later removed by treating sodium methoxide in THF |
| 23 | 83 | 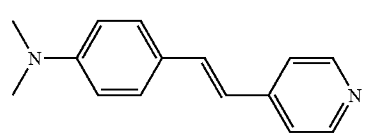 | B | 75 | Acetic anhydride heating condition |
| 24 | 10 | 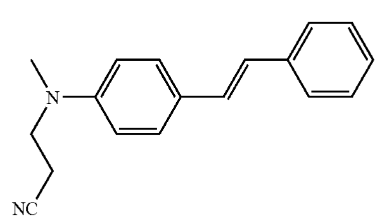 | C | 95 | 50° C. Heating for 6 hours, THF as solvent |

TABLE 1-continued

Summary of 68 compounds structure, synthetic method, purity and synthetic notes

| Num. | Code | structure | method | % purity | Synthetic note |
|---|---|---|---|---|---|
| 25 | 23 | 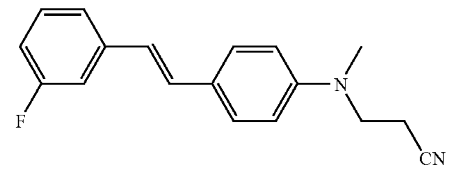 | C | 98 | 50° C. Heating for 6 hours, THF as solvent |
| 26 | 90 | 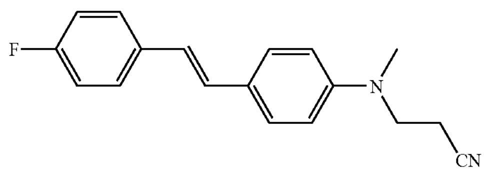 | C | 99 | 50° C. Heating for 6 hours, THF as solvent |
| 27 | 23I | 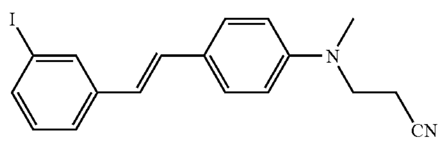 | C | 99 | 50° C. Heating for 6 hours, THF as solvent |
| 28 | 95 | 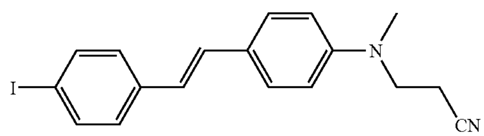 | C | 99 | 50° C. Heating for 6 hours, THF as solvent |
| 29 | 23B | 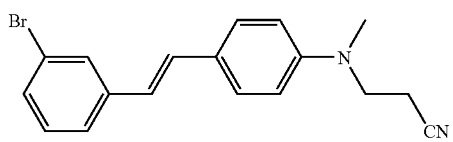 | C | 99 | 50° C. Heating for 6 hours, THF as solvent |
| 30 | 22 | 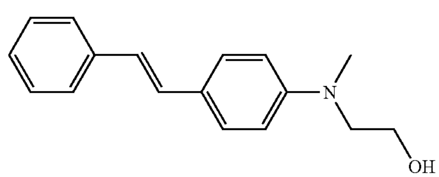 | C | 98 | |
| 31 | 24 | 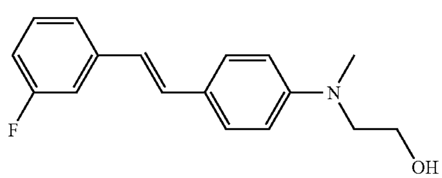 | C | 99 | |
| 32 | 27 | 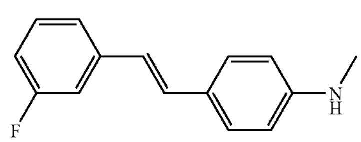 | C | 90 | |
| 33 | 84 | 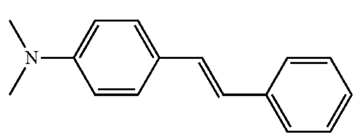 | C | 99 | |

TABLE 1-continued

Summary of 68 compounds structure, synthetic method, purity and synthetic notes

| Num. | Code | structure | method | % purity | Synthetic note |
|------|------|-----------|--------|----------|----------------|
| 34 | 66 | 2-methoxy-1-(pyridin-4-yl-vinyl)naphthalene | B | 99 | microwave reaction |
| 35 | 68 | 2-methoxy-1-styryl-naphthalene | C | 91 | |
| 36 | 71 | 4-methoxy-1-(pyridin-4-yl-vinyl)naphthalene | B | 60 | microwave reaction |
| 37 | 73 | 4-methoxy-1-styryl-naphthalene | C | 90 | |
| 38 | 63 | 2-(pyridin-4-yl-vinyl)naphthalene | B | 90 | microwave reaction |
| 39 | 85 | 4-morpholinyl-styryl-benzene | C | 85 | |
| 40 | 86 | 4-imidazolyl-styryl-benzene | C | 92 | |
| 41 | 87 | 4-(2-hydroxyethylamino)-stilbene | C | 82 | |

TABLE 1-continued
Summary of 68 compounds structure, synthetic method, purity and synthetic notes
| Num. | Code | structure | method | % purity | Synthetic note |
|---|---|---|---|---|---|
| 42 | 88 | 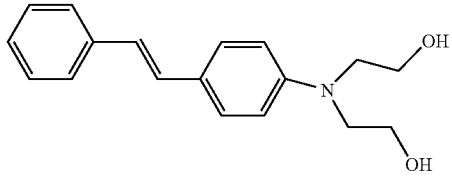 | C | 97 | |
| 43 | 76 | 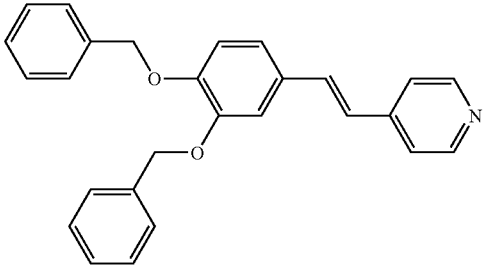 | B | 60 | |
| 44 | 77 | 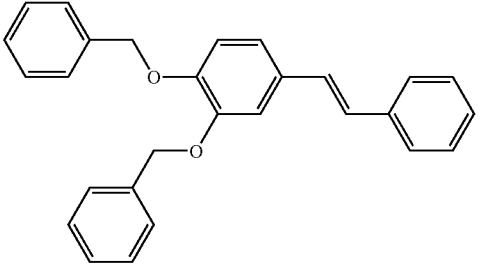 | C | 92 | microwave reaction |
| 45 | 78 | 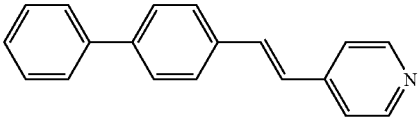 | B | 90 | |
| 46 | 21 | 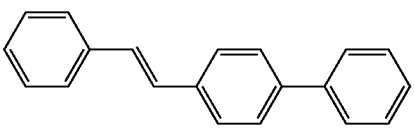 | C | 94 | |
| 47 | 96 | 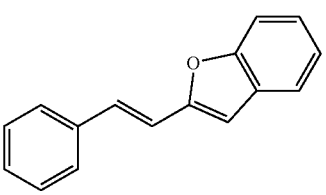 | C | 91 | |
| 48 | 97 | 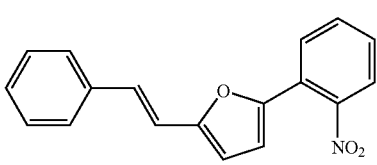 | C | 95 | |
| 49 | 98 | 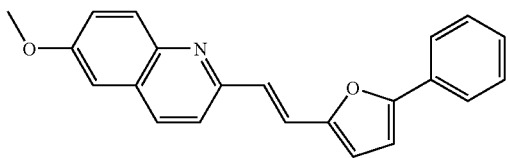 | C | 95 | |

TABLE 1-continued
Summary of 68 compounds structure, synthetic method, purity and synthetic notes
| Num. | Code | structure | method | % purity | Synthetic note |
|---|---|---|---|---|---|
| 50 | 99 | 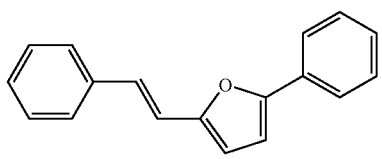 | C | 98 | |
| 51 | 59 | 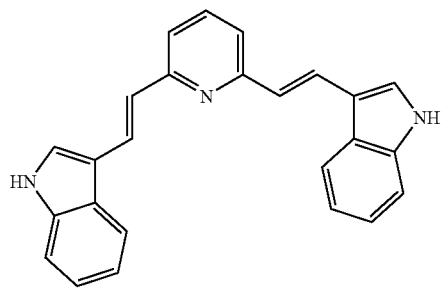 | D | 70 | Wittig reagent was made from bis-2,6-dibromomethyl pyridine |
| 52 | 52 | 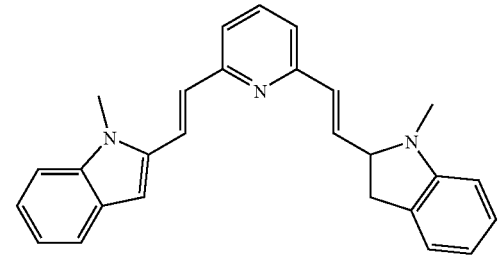 | C | 90 | phosphonate was made from bis-2,6-dibromomethyl pyridine |
| 53 | 89 | 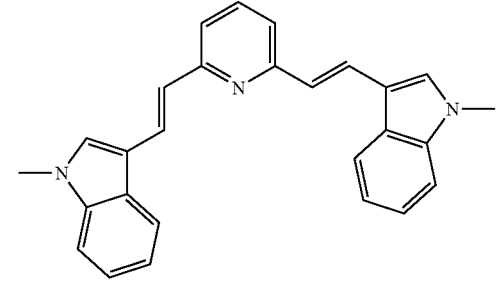 | C | 80 | phosphonate was made from bis-2,6-dibromomethyl pyridine |
| 54 | 61 | 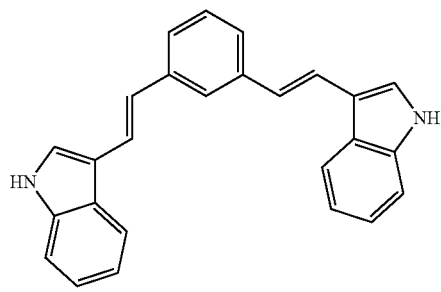 | D | 85 | |

TABLE 1-continued

Summary of 68 compounds structure, synthetic method, purity and synthetic notes

| Num. | Code | structure | method | % purity | Synthetic note |
|---|---|---|---|---|---|
| 55 | 54 | 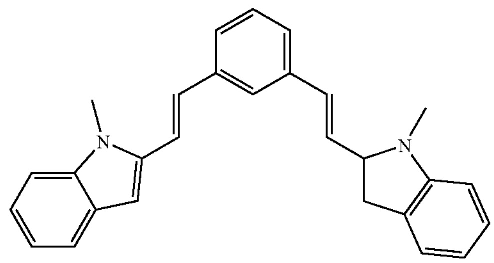 | C | 99 | |
| 56 | 55 | 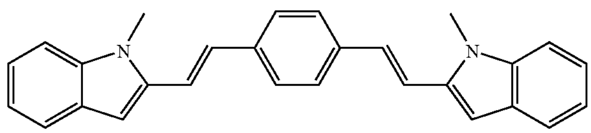 | C | 81 | |
| 57 | 72 | 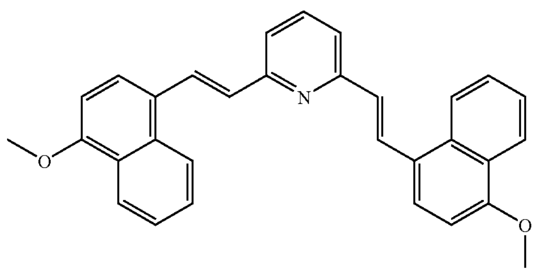 | C | 50 | phosphonate was made from bis-2,6-dibromomethyl pyridine |
| 58 | 67 | 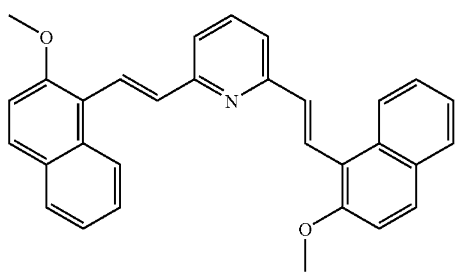 | C | 95 | phosphonate was made from bis-2,6-dibromomethyl pyridine |
| 59 | 74 | 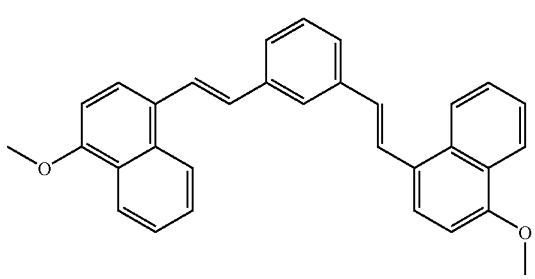 | C | 97 | |
| 60 | 75 | 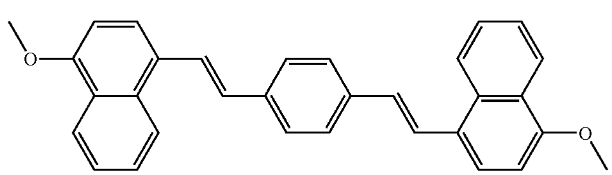 | C | 89 | |

TABLE 1-continued

Summary of 68 compounds structure, synthetic method, purity and synthetic notes

| Num. | Code | structure | method | % purity | Synthetic note |
|---|---|---|---|---|---|
| 61 | 69 | 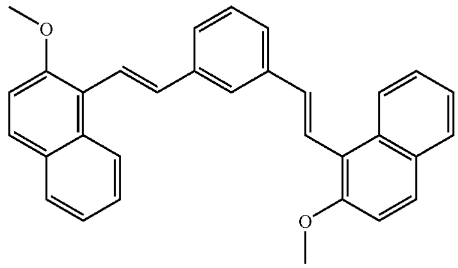 | C | 85 | |
| 62 | 70 | 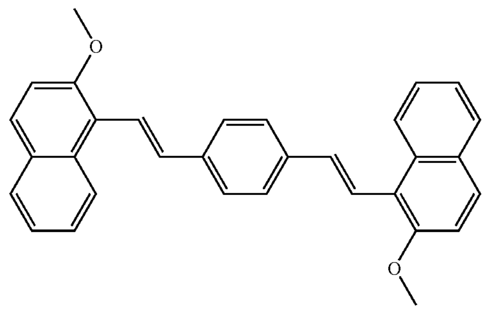 | C | 93 | |
| 63 | 7 | 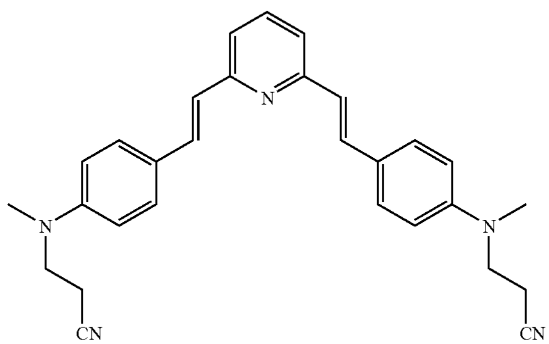 | C | 95 | 50° C. Heating for 6 hours, THF as solvent |
| 64 | 12 | 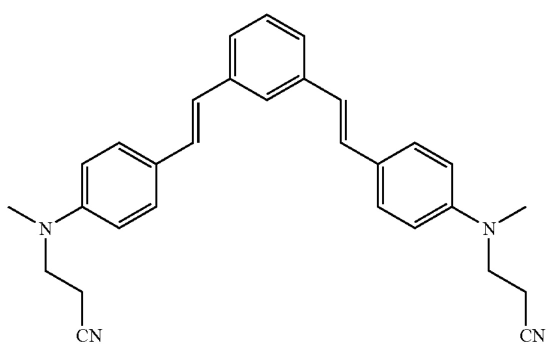 | C | 86 | 50° C. Heating for 6 hours, THF as solvent |
| 65 | 25 | 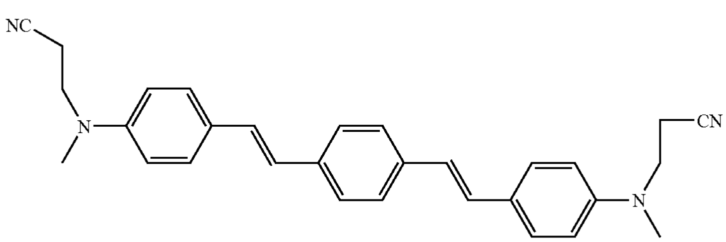 | C | 85 | 50° C. Heating for 6 hours, THF as solvent |

TABLE 1-continued

Summary of 68 compounds structure, synthetic method, purity and synthetic notes

| Num. | Code | structure | method | % purity | Synthetic note |
|---|---|---|---|---|---|
| 66 | 14 | 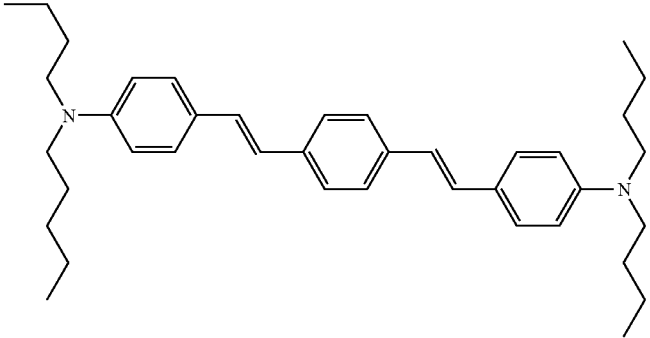 | C | 95 | |

While thioflavin T or S (ThT or ThS) and Congo red (CR) are widely used for amyloid detection agents, neither of them penetrates the brain blood barrier (BBB). Several compounds have been published as new imaging agents for detecting amyloid plaque in vitro and in vivo; however, many of them are limited by the scaffold of Congo red and thioflavin T[7-13]. Previous research on fluorescent styryl compounds has proved that this scaffold has great potential in recognizing many different biological analytes including amyloid plaque[14, 15], nucleic acid[16] as well as for staining specific organelle in live cells[17, 18]. The present invention provides a group of novel fluorescent compounds based on the styryl scaffold. The preliminary data show promising results of these compounds as new imaging agents for misfolded proteins such as amyloid plaque both in vitro and in vivo.

Preparation of Amyloid Insulin Fibrils

Bovine insulin stock solution was freshly prepared at 1 mg/mL in HCl solution (40 mM). Storage of solutions was avoided to prevent any possible aggregation under storage conditions. The solution was incubated in 50° C. overnight to form amyloid insulin fibrils. The formation of insulin amyloid fibrils was further confirmed using an atomic force microscope.

Fluorescent Measurement Using Gemini XS Fluorescent Plate Reader

Generally for primary screening, 350 nm, 400 nm, 450 nm, 500 nm, and 550 nm excitation wavelengths were chosen and emission wavelengths were scanned. Grainer 96 well black polypropylene plates were used. 1 mg/mL insulin amyloid fibril solution was used in the measurement. The final concentration of compound was 10 mM.

TABLE 2

In vitro solution assay result.

| compound | Ex | Em | Insulin fold |
|---|---|---|---|
| 7 | 500 | 630 | 25 |
| 8 | 400 | 500 | 10 |
| 9 | 400 | 510 | 25 |
| 10 | 350 | 420 | 14 |
| 11 | 500 | 580 | 3 |
| 12 | 400 | 470 | 2 |
| 16 | 500 | 600 | 20 |
| 17 | 500 | 630 | 2 |
| 18 | 450 | 530 | 3 |
| 20 | 400 | 520 | 30 |

TABLE 2-continued

In vitro solution assay result.

| compound | Ex | Em | Insulin fold |
|---|---|---|---|
| 21 | 350 | 430 | 1 |
| 22 | 350 | 440 | 160 |
| 23 | 350 | 450 | 40 |
| 24 | 350 | 450 | 150 |

Compound 1 mM final concentration. Fibril Insulin 1 mg/mL aqueous solution pH = 1.4

(e) Brain Imaging Data

Human Alzheimer Brain Slide Co-staining by DAB and Our Compounds

A complete DAB (3,3'-diaminobenzidine) staining was first carried out by primary antibody and biotinylated second antibody binding using Vector M.O.M immunodetection kit (BMK 2202). It was then followed by peroxidase binding using Vectastain ABC kit (PK-6100) and completed by peroxidase substrate binding using Vector DAB substrate kit (SK-4100). The established protocols[19] were followed in the experiments. The DAB stained brain slides were then stained by our synthetic compounds in 10 μM concentration. The fluorescent imaging was carried out using a Leica confocal DMIRE2 fluorescence microscope. DAB staining was visualized in bright field. Our compounds' staining was imaged using DAPI (ex 360/40, em 470/40, dichromatic filter 400), FITC (ex 480/40, em 527/30, dichromatic filter 505) or Cy3 (ex 545/30, em 610/75, dichromatic filter 565) band pass filters cubes (Chroma, www.chroma.com).

A method for visualization of misfolded proteins such as amyloid plaques prior to clinical impairment will be very important for prophylactic treatment for Alzheimer's disease (AD). Recent studies suggest positron emission tomography (PET) ligands can be used to directly image β-amyloid associated with Alzheimer's disease (AD). A large library of styryl-based dyes have been screened in vitro for amyloid binding ability. It was found that several of these dyes are highly effective at labeling amyloid plaques in tissue sections of AD patients and from AD model mice (see FIG. 6). We have further tested their blood-brain barrier permeability and their ability to label amyloid plaques both in tissue sections and in vivo using AD model transgenic mice (see FIGS. 3 and 4). The most effective compounds tested so far are 23, 8 and 8F. In addition some mice were subject to in vivo transcranial two-photon microscopy imaging (see FIG. 5). No labeling was seen in control animals will in AD model mice specific labeling of all amyloid plaques was observed. No toxicity of any of the compounds used was evident. These compounds allow for the in vivo detection of amyloid plaques and potentially can be developed into a suitable PET ligand for human use.

Methods used: Five groups each of 6-month-old PS/APP Tg mice were tested (which have abundant amyloid plaques) with the compounds of the present invention. The mice received an intraperitoneal injection of compounds 23, 8 or 8F (30 μg/gram). They were sacrificed 24 hours later by ip injection of sodium pentobarbital (150 mg/kg). All animals were transcardially perfused with 20 ml of 0.1 M phosphate buffered saline (pH 7.4) with the addition of heparin followed by 80 ml of 4% formaldehyde in 0.1 M phosphate buffer. The brain was removed from the skull, cryoprotected using increasing concentrations of sucrose, and cut into serial 40-μm-thick coronal section on a freezing microtome (Leica SM2400, Nussloch, Germany). Anti-amyloid β immunohistochemistry was performed on free-floating sections, using our previously published protocols[20-23]. In brief, endogenous peroxidase activity was quenched in a bath with 0.3% $H_2O_2$ for 30 min. Unspecific staining was blocked by incubation in the blocking solution provided as a part of "Mouse on mouse" kit (Vector Elite staining kit, Vector Laboratories, Burlingame, Calif.). This procedure allows for detection of antigens in murine tissue using mouse mAb avoiding substantial background. Concentration of all mAbs was 0.25 mg/ml with the total concentration of protein in a stock solution of 1 mg/ml as assessed by a Coomasie colorimetric assay. 1:2000 dilution of the stock solution was used. Primary antibodies were applied for 30 minutes followed by thorough washing and the anti-mouse IgG biotinylated secondary antibody according to the kit manufacturer instruction. For fluorescent microscopy sections were incubated with streptavidin conjugated with Cy3 (1:400; Sigma, St. Louis Mo.) whereas for light microscopy they were incubated with avidin-horseradish peroxidase complex and developed using 3,3'-diaminobenzidine kit with nickel ammonium sulfate (Vector Laboratories, Burlingame, Calif.). Following immunostaining, sections were carried on slides, air-dried, and cover-slipped. Some of sections were optionally stained with Thioflavin-S, which allowed for simultaneous demonstration of all three stainings including with 23, 8, 8F, Cy3, and Thioflavin-S using fluorescent microscope with different filter combinations. Attached to slides, the sections were immersed for six minutes into 0.5% Thioflavin-S solution in distilled water and differentiated by dipping a few times in 80% alcohol. Slides were washed in distilled water and covered with 9:1 mixture of glycerol with PBS.

Sections from control animals which did not received ip injection of compounds 23, 8 and 8F were immunostained with anti-Aβ and DAB for light microscopy or double stained with anti Aβ mAb and Cy3 and then either with Thioflavin-S or with compounds of the present invention for double fluorescent microscope detection. Direct staining with either 23, 8 or 8F was performed by immersion of slides in ethanol solution of this dye for 10 minutes and differentiation 80% ethanol in 0.2% NaOH for two minutes. Sections were then washed with distilled water and cover with PBS-glycerol. Separate set of section was stained only with Thioflavin-S or compounds of the present invention with or without 30 minutes pretreatment with 80% formic acid.

Sections from AD patient's cases were deparaffinized and stained either with Thioflavin-S, 23, 8 or 8F, or immunostained. For immunohistochemistry sections were pretreated with 80% formic acid for 15 minutes. Endogenous peroxidase activity was quenched by 30 min bath in 0.3% $H_2O_2$ in methanol. Sections were then washed and blocked with 10% fetal bovine serum for 30 minutes. Aβ plaques were detected as described above.

For in vivo detection of amyloid plaques using transcranial two-photon microscopy three APP/PS1 mice received intraperitoneal injection of compound 23 (20 μg/gram of body weight) 24 hours prior to imaging, using methods as we have previously published[24]. For in vivo transcranial two-photon microscopy imaging animals were anesthetized by intraperitoneal injection of Ketamine HCl 0.12 mg/gram of body weight and Xylazine 0.016 mg/gram diluted in distilled water. Under aseptic conditions skin over the skull was opened with midline excision and the periosteum was removed. A 2 mm×2 mm window in a skull bone was opened from the point located 1 mm to the back of the bregma and proceeding backward and 1 mm laterally from the midline suture and proceeding laterally. Bone was carefully removed using a high-speed drill (Fine Science Tools, Foster City, Calif., USA). To avoid damaging the underlying cortex by friction-induced heat, a cold sterile saline was administered to the skull periodically, and drilling was intermittently halted to permit heat dissipation. Using a micro-surgical blade (Surgistar no. 6400) skull thickness was further reduced to about 30-50 μm. Respiration-induced movements during imaging were reduced by fixing the skull with a cyanoacrylic glue (Elmer Products no. KG-585) to a custom made stainless steel plate 400 mm thick with a central opening for skull access. The plate was screwed to two lateral bars located on both sides of the mouse head and fixed to a metal base. In vivo imaging was performed using the Biorad Multiphoton system (MRC-1024m equipped with long working distance objectives ×10 and ×60. Two-photon fluorescence was generated with 750 nm excitation from a mode-locked Ti:Saphhire laser (Tsunami, Spectra-Physics, Mountain View, Calif.). Light waves emitted by compound 23 were collected in the range of 380 to 680 nm. Three-dimensional volumes were acquired by a stack of x-y sections starting at the surface of the thinned skull to a 200 μm depth inside the cortex[25]. This is shown in FIG. 9. A similar experiment was performed using compound 8 and this is shown in FIG. 10. Following in vivo two-photon imaging, animals were sacrificed by ip injection of sodium pentobarbital and transcardialay perfused as described above.

Importantly, these compounds have been tested for any potential toxicity using standard MTT assays (see FIG. 11). The effect of 1-50 μmol/L concentrations of compounds 8 and 23 on the viability of the SK-N-SH human neuroblastoma cell line (American Type Culture Collection, Manassas, Va.) was compared to the well established neurotoxicity of Aβ1-42 in this cell line model. Viability of SK-N-SH cells cultured in a flat-bottom, 96-well microtiter plates in the presence of peptides for two days, was assessed using the MTT metabolic assay according to the manufacturer's manual (Roche Molecular Biochemicals, Indianapolis, Ind.). There is no toxicity evident with compounds 8 and 23 at a concentration of 1 to 50 μM versus control untreated cells, whereas Aβ1-42 showed the expected toxicity (see FIG. 11).

As described above, the compounds of the present invention and compounds derived from these compounds have been found to be useful for imaging misfolded proteins in PET probes and MRI probes. They can be safely injected into living animals to provide in vivo imaging of misfolded proteins in the brain, thus making it possible to diagnose diseases resulting from protein misfolding, including but not limited to Alzheimer's Disease, Type II diabetes, Parkinson's Disease, Huntington's Disease and Creutzfeldt-Jakob disease.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus, the expressions "means to . . . " and "means for . . . ", or any method step language, as may be found in the specification above and/or in the claims below, followed by a functional statement, are intended to define and cover whatever structural, physical, chemical, or electrical element or structure, or whatever method step, which may now or in the future exist which carries out the recited functions, whether or not precisely equivalent to the embodiment or embodiments disclosed in the specification above, i.e., other means or steps for carrying out the same function can be used; and it is intended that such expressions be given their broadest interpretation.

REFERENCES

Agdeppa, E. D. et al., "Binding characteristics of radiofluorinated 6-dialkylamino-2-naphthylethylidene derivatives as positron emission tomography imaging probes for beta-amyloid plaques in Alzheimer's disease", *J Neurosci* 21, art. no.-RC189 (2001)

Bayer, T. A. et al., "Key factors in Alzheimer's disease: beta-amyloid precursor protein processing, metabolism and intraneuronal transport", *Brain Pathol*, 11:1-11 (2001)

Chang, T. Y. R., G. R., "Combinatorial fluorescent library based on the styryl scaffold", US patent applied, (2002) Protocols are available at www.vectorlabs.com.

Chang, Y. T., "Styryl dyes with linker", US patent applied (2004).

Clark, C. M., "Neurodegenerative dementias: clinical features and pathological mechanisms", (McGraw-Hill, New York, 2000)

Hardy, J. & Selkoe, D. J. Medicine, "The amyloid hypothesis of Alzheimer's disease: Progress and problems on the road to therapeutics", *Science*, 297:353-356 (2002)

Kelly, J. W., Alternative conformations of amyloidogenic proteins govern their behavior", *Curr Opin Struc Biol*, 6: 11-17 (1996).

Kung, H. F. et al., "Novel stilbenes as probes for amyloid plaques", *J Am Chem Soc*, 123:12740-12741 (2001)

Kung, M. P. et al., "IMPY: an improved thioflavin-T derivative for in vivo labeling of beta-amyloid plaques", *Brain Res* 956:202-210 (2002)

Lee, J. W., Jung, M., Rosania, G. R. & Chang, Y. T., "Development of novel cell-permeable DNA sensitive dyes using combinatorial synthesis and cell-based screening" *Chem Commun*, 1852-1853 (2003)

Li, Q. A. et al., "Solid-phase synthesis of styryl dyes and their application as amyloid sensors", *Angew Chem Int Edit*, 43:6331-6335 (2004)

Mathis, C. A. et al., "Synthesis and evaluation of C-11-labeled 6-substituted 2-arylbenzothiazoles as amyloid imaging agents", *J Med Chem*, 46:2740-2754 (2003)

Murphy, R. M., "Peptide aggregation in neurodegenerative disease", *Annu Rev Biomed Eng*, 4:155-174 (2002)

Rosania, G. R., Lee, J. W., Ding, L., Yoon, H. S. & Chang, Y. T., "Combinatorial approach to organelle-targeted fluorescent library based on the styryl scaffold", *J Am Chem Soc* 125:1130-1131 (2003)

Sadowski, M. et al. "Amyloid-beta deposition is associated with decreased hippocampal glucose metabolism and spatial memory impairment in APP/PS1 mice", *J Neuropath Exp Neur* 63:418-428 (2004)

Sadowski, M. et al., "A synthetic peptide blocking the apolipoprotein E/beta-amyloid binding mitigates beta-amyloid toxicity and fibril formation in vitro and reduces beta-amyloid plaques in transgenic mice", *Am J Pathol*, 165: 937-948 (2004)

Sadowski, M. et al., "Links between the pathology of Alzheimer's disease and vascular dementia", *Neurochem Res*, 29:1257-1266 (2004)

Sadowski, M. et al., "Targeting prion amyloid deposits in vivo", *J Neuropath Exp Neur*, 63:775-784 (2004)

Sigurdsson, E. M. et al. "An attenuated immune response is sufficient to enhance cognition in an Alzheimer's disease mouse model immunized with amyloid-beta derivatives", *J Neurosci*, 24:6277-6282 (2004)

Sipe, J. D. & Cohen, A. S., "Review: History of the amyloid fibril", *J Struct Biol*, 130:88-98 (2000)

Skovronsky, D. M. et al., "In vivo detection of amyloid plaques in a mouse model of Alzheimer's disease", *P Natl Acad Sci USA*, 97:7609-7614 (2000)

Styren, S. C., Hamilton, R. L., Styren, G. C. & Klunk, W. K., "X-34, a fluorescent derivative of Congo red: A novel histochemical stain for Alzheimer's disease pathology", *J Histochem Cytochem*, 48:1223-1232 (2000)

Wisniewski, T., "Prion related diseases", *emedicine* emedicine.com/neuro/topic662.htm. (2002)

Zhuang, Z. P. et al., "Radioiodinated styrylbenzenes and thioflavins as probes for amyloid aggregates", *J Med Chem*, 44:1905-1914 (2001)

What is claimed is:

1. A compound of Formula II

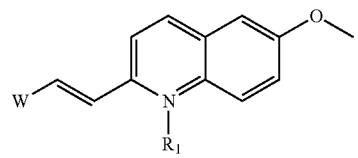

wherein R1=none, or —CH$_2$CH$_2$CH$_2$CH$_2$SO$_3$; and W=substituted or unsubstituted biphenyl, or naphthyl.

2. A method for staining amyloid plaque, comprising incubating brain slices in a solution of a compound according to claim 1, and imaging the brain slices by laser scanning confocal microscopy.

3. The fluorescent styryl compound of claim 1 which is

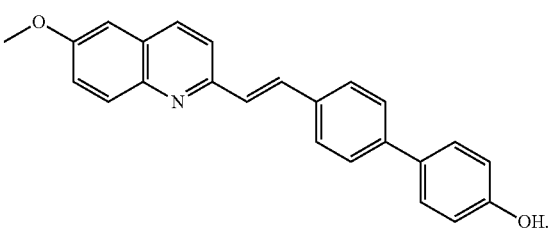

* * * * *